(12) United States Patent
Takahashi

(10) Patent No.: US 11,096,645 B2
(45) Date of Patent: *Aug. 24, 2021

(54) BONE MINERAL INFORMATION ACQUISITION APPARATUS, BONE MINERAL INFORMATION ACQUISITION METHOD, AND BONE MINERAL INFORMATION ACQUISITION PROGRAM

(71) Applicant: FUJIFILM Corporation, Tokyo (JP)

(72) Inventor: Tomoyuki Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 170 days.

This patent is subject to a terminal disclaimer.

(21) Appl. No.: 16/417,935

(22) Filed: May 21, 2019

(65) Prior Publication Data

US 2019/0374185 A1 Dec. 12, 2019

(30) Foreign Application Priority Data

Jun. 8, 2018 (JP) .............................. JP2018-109990

(51) Int. Cl.
*A61B 6/00* (2006.01)
*A61B 6/02* (2006.01)
(Continued)

(52) U.S. Cl.
CPC ............ *A61B 6/505* (2013.01); *A61B 5/7275* (2013.01); *A61B 6/025* (2013.01); *A61B 6/4291* (2013.01);
(Continued)

(58) Field of Classification Search
CPC ....... A61B 5/7275; A61B 6/505; A61B 6/025; A61B 6/544; A61B 6/4291; A61B 6/5235;
(Continued)

(56) References Cited

U.S. PATENT DOCUMENTS

| 5,418,373 A | 5/1995 | Shimura |
| 10,235,766 B2 | 3/2019 | Naito |

(Continued)

FOREIGN PATENT DOCUMENTS

| JP | H6-66777 A | 3/1994 |
| JP | 2004-147863 A | 5/2004 |

(Continued)

OTHER PUBLICATIONS

Japanese Office Action dated Jun. 29, 2021, for corresponding Japanese Application No. 2018-109990 with English translation.

*Primary Examiner* — Marcos L Torres

(74) *Attorney, Agent, or Firm* — Birch, Stewart, Kolasch & Birch, LLP

(57) ABSTRACT

A body thickness estimation unit estimates a body thickness of a subject for each pixel of at least one radiographic image among a plurality of radiographic images each of which includes a primary ray component and a scattered ray component, on the basis of the at least one radiographic image. A bone part pixel value acquisition unit acquires a bone part pixel value which is a pixel value of a bone region of the subject, on the basis of the at least one radiographic image. An information acquisition unit acquires bone mineral information indicating a bone mineral content of the bone region for each pixel of the bone region on the basis of imaging conditions in a case in which the at least one radiographic image has been acquired, the body thickness for each pixel, and the bone part pixel value.

19 Claims, 12 Drawing Sheets

(51) Int. Cl.
*G06T 11/00* (2006.01)
*A61B 5/00* (2006.01)

(52) U.S. Cl.
CPC ............ *A61B 6/463* (2013.01); *A61B 6/5235* (2013.01); *A61B 6/5282* (2013.01); *A61B 6/544* (2013.01); *G06T 11/005* (2013.01)

(58) Field of Classification Search
CPC ..... A61B 6/5282; A61B 6/463; G06T 11/005; G06T 11/008
See application file for complete search history.

(56) References Cited

U.S. PATENT DOCUMENTS

| 2011/0036360 | A1* | 2/2011 | Lang | G06T 7/20 |
| | | | | 128/898 |
| 2013/0343521 | A1* | 12/2013 | Lee | A61B 6/5241 |
| | | | | 378/62 |
| 2018/0028139 | A1 | 2/2018 | Kuwabara | |

FOREIGN PATENT DOCUMENTS

| JP | 2008-167949 A | 7/2008 |
| JP | 2010-167159 A | 8/2010 |
| JP | 2014-054301 A | 3/2014 |
| JP | 2015-043959 A | 3/2015 |
| JP | 2015-084805 A | 5/2015 |
| JP | 2018-15453 A | 2/2018 |

\* cited by examiner

BONE STRENGTH
HIGH
LOW

BONE MINERAL CONTENT
LARGE
SMALL

BONE MINERAL INFORMATION ACQUISITION APPARATUS, BONE MINERAL INFORMATION ACQUISITION METHOD, AND BONE MINERAL INFORMATION ACQUISITION PROGRAM

CROSS REFERENCE TO RELATED APPLICATIONS

The present application claims priority under 35 U.S.C. § 119 to Japanese Patent Application No. 2018-109990 filed on Jun. 8, 2018. The above application is hereby expressly incorporated by reference, in its entirety, into the present application.

BACKGROUND

Technical Field

The present disclosure relates to a bone mineral information acquisition apparatus, a bone mineral information acquisition method, and a bone mineral information acquisition program that acquire bone mineral information using a radiographic image including a bone.

Related Art

Dual X-ray absorptiometry (DXA) has been known as a representative bone mineral quantitation method used to diagnose bone density in a bone disease such as osteoporosis. The DXA method calculates bone mineral content from the pixel values of radiographic images obtained by imaging with radiations having two types of energy levels, using the fact that radiation which is incident on the human body and is transmitted through the human body is attenuated by a mass attenuation coefficient $\mu$ ($cm^2/g$) depending on a substance (for example, bone) forming the human body, the density $\rho$ ($g/cm^3$) of the substance, and the thickness t (cm) of the substance.

In addition, a radiography apparatus has been known which comprises two radiation detectors that include a plurality of pixels accumulating charge corresponding to emitted radiation and are provided so as to be stacked. Further, a technique has been known which measures the bone mineral content of a subject using each electric signal corresponding to the amount of radiation emitted to each radiation detector in this type of radiography apparatus (see JP2018-015453A).

However, in a case in which radiographic images are acquired, scattered rays are generated due to the scattering of radiation in the subject. In the DXA method, the subject is irradiated with radiation such that the influence of scattered rays is reduced. In order to acquire bone mineral information using the DXA method, a dedicated apparatus for irradiating the subject with radiation is required as described above. Therefore, it is difficult to use the existing facilities. In addition, since the DXA method calculates bone mineral content for each bone, it is difficult to evaluate bone mineral information for each part of the bone.

SUMMARY OF THE INVENTION

The present disclosure has been made in view of the above-mentioned problems and an object of the present disclosure is to provide a technique that can acquire bone mineral information using the existing facilities.

According to an aspect of the present disclosure, there is provided a bone mineral information acquisition apparatus comprising: a body thickness estimation unit that estimates a body thickness of a subject including a bone part and a soft part for each pixel of at least one radiographic image among a plurality of radiographic images each of which is acquired by radiations transmitted through the subject and includes a primary ray component and a scattered ray component, on the basis of the plurality of radiographic images; a bone part pixel value acquisition unit that acquires a bone part pixel value which is a pixel value of a bone region of the subject, on the basis of the at least one radiographic image; and an information acquisition unit that acquires bone mineral information indicating a bone mineral content of the bone region for each pixel of the bone region on the basis of imaging conditions in a case in which the at least one radiographic image has been acquired, the body thickness for each pixel, and the bone part pixel value.

The bone mineral information acquisition apparatus according to the aspect of the present disclosure may further comprise an image acquisition unit that moves a radiation source relative to a detection unit, and acquires, as the plurality of radiographic images, a plurality of projection images corresponding to a plurality of radiation source positions by the movement of the radiation source, the projection images being generated by tomosynthesis imaging in which the subject is irradiated with the radiation, at the plurality of radiation source positions; and a reconstruction unit that reconstructs the plurality of radiographic images to generate a plurality of tomographic images of a plurality of tomographic planes of the subject. The bone part pixel value acquisition unit may acquire a thickness of the bone part in a direction orthogonal to the tomographic plane on the basis of the bone region included in the plurality of tomographic images, and acquire the bone part pixel value on the basis of the thickness of the bone part.

The bone mineral information acquisition apparatus according to the aspect of the present disclosure may further comprise an image acquisition unit that acquires the plurality of radiographic images generated by irradiating the subject with the radiation from a plurality of mutually orthogonal directions. The bone part pixel value acquisition unit may acquire a thickness of the bone part in an imaging direction of one radiographic image among the plurality of radiographic images on the basis of the bone region included in the plurality of radiographic images, and acquire the bone part pixel value on the basis of the thickness of the bone part.

In the bone mineral information acquisition apparatus according to the aspect of the present disclosure, the information acquisition unit may acquire the bone mineral information by converting the bone part pixel value into a pixel value of the bone region included in the radiographic image acquired on the basis of a reference imaging condition.

In the bone mineral information acquisition apparatus according to the aspect of the present disclosure, the reference imaging condition may be a tube voltage that is applied to a radiation source in a case in which the at least one radiographic image is acquired.

In the bone mineral information acquisition apparatus according to the aspect of the present disclosure, the information acquisition unit may acquire the bone mineral information by converting the bone part pixel value on the basis of a correction coefficient corresponding to at least one of information on the reference imaging condition, information on beam hardening corresponding to the body thickness, or information on whether a scattered ray removal grid is present during imaging.

The bone mineral information acquisition apparatus according to the aspect of the present disclosure may further comprise a display controller that displays related information, which is related to the bone mineral information, on a display unit.

The related information that is related to the bone mineral information includes new information calculated from the bone mineral information and new information calculated from information other than the bone mineral information. In addition, the related information may be the bone mineral information.

In the bone mineral information acquisition apparatus according to the aspect of the present disclosure, the display controller may displays, as the related information, a composite image obtained by superimposing the bone mineral information on a soft part image indicating a soft region of the subject or the at least one radiographic image on the display unit, the soft part image being acquired from the at least one radiographic image.

In the bone mineral information acquisition apparatus according to the aspect of the present disclosure, the display controller may display bone strength calculated from the bone mineral information as the related information on the display unit.

In the bone mineral information acquisition apparatus according to the aspect of the present disclosure, in a case in which the subject includes a plurality of bones, the display controller may display the related information acquired for each bone on the display unit.

In the bone mineral information acquisition apparatus according to the aspect of the present disclosure, the display controller may display the related information on a partial region in the bone region on the display unit.

In the bone mineral information acquisition apparatus according to the aspect of the present disclosure, the partial region may be a cancellous bone region in the bone region.

In the bone mineral information acquisition apparatus according to the aspect of the present disclosure, in a case in which the subject includes a plurality of bones, the display controller may display a comparison result of the bone mineral information between the bones as the related information on the display unit.

In the bone mineral information acquisition apparatus according to the aspect of the present disclosure, the display controller may display a comparison result of the bone mineral information between partial regions in the bone region as the related information on the display unit.

In the bone mineral information acquisition apparatus according to the aspect of the present disclosure, the display controller may display a comparison result between the bone mineral information and past bone mineral information acquired at different dates and times for the same subject as the related information on the display unit.

In the bone mineral information acquisition apparatus according to the aspect of the present disclosure, in a case in which the bone region is a vertebra region, the display controller may display, as the related information, information indicating a bone fracture risk which is generated from spinal alignment and the bone mineral information on the display unit.

The bone mineral information acquisition apparatus according to the aspect of the present disclosure may further comprise a related information generation unit that generates the related information.

According to another aspect of the present disclosure, there is provided a bone mineral information acquisition method comprising: estimating a body thickness of a subject including a bone part and a soft part for each pixel of at least one radiographic image among a plurality of radiographic images each of which is acquired by radiations transmitted through the subject and includes a primary ray component and a scattered ray component, on the basis of the plurality of radiographic images; acquiring a bone part pixel value which is a pixel value of a bone region of the subject, on the basis of the at least one radiographic image; and acquiring bone mineral information indicating a bone mineral content of the bone region for each pixel of the bone region on the basis of imaging conditions in a case in which the at least one radiographic image has been acquired, the body thickness for each pixel, and the bone part pixel value.

A program that causes a computer to perform the bone mineral information acquisition method according to the aspect of the present disclosure may be provided.

A bone mineral information acquisition apparatus according to another aspect of the present disclosure comprises a memory that stores commands to be executed by a computer and a processor configured to execute the stored commands. The processor performs: a process of estimating a body thickness of a subject including a bone part and a soft part for each pixel of at least one radiographic image among a plurality of radiographic images each of which is acquired by radiations transmitted through the subject and includes a primary ray component and a scattered ray component, on the basis of the plurality of radiographic images; acquiring a bone part pixel value which is a pixel value of a bone region of the subject, on the basis of the at least one radiographic image; and acquiring bone mineral information indicating a bone mineral content of the bone region for each pixel of the bone region on the basis of imaging conditions in a case in which the at least one radiographic image has been acquired, the body thickness for each pixel, and the bone part pixel value.

According to the present disclosure, the body thickness of the subject is estimated for each pixel of at least one radiographic image among a plurality of radiographic images and the bone part pixel value which is the pixel value of the bone region of the subject is acquired on the basis of the at least one radiographic image. The bone mineral information indicating the bone mineral content of the bone region for each pixel of the bone region is acquired on the basis of the imaging conditions in a case in which the at least one radiographic image has been acquired, the body thickness for each pixel, and the bone part pixel value. Therefore, it is possible to acquire the bone mineral information without using a dedicated apparatus unlike the DXA method. In addition, since the bone mineral information is acquired for each pixel of the bone region, it is possible to evaluate the bone mineral information for each part of the bone.

DETAILED DESCRIPTION

Figure 1:
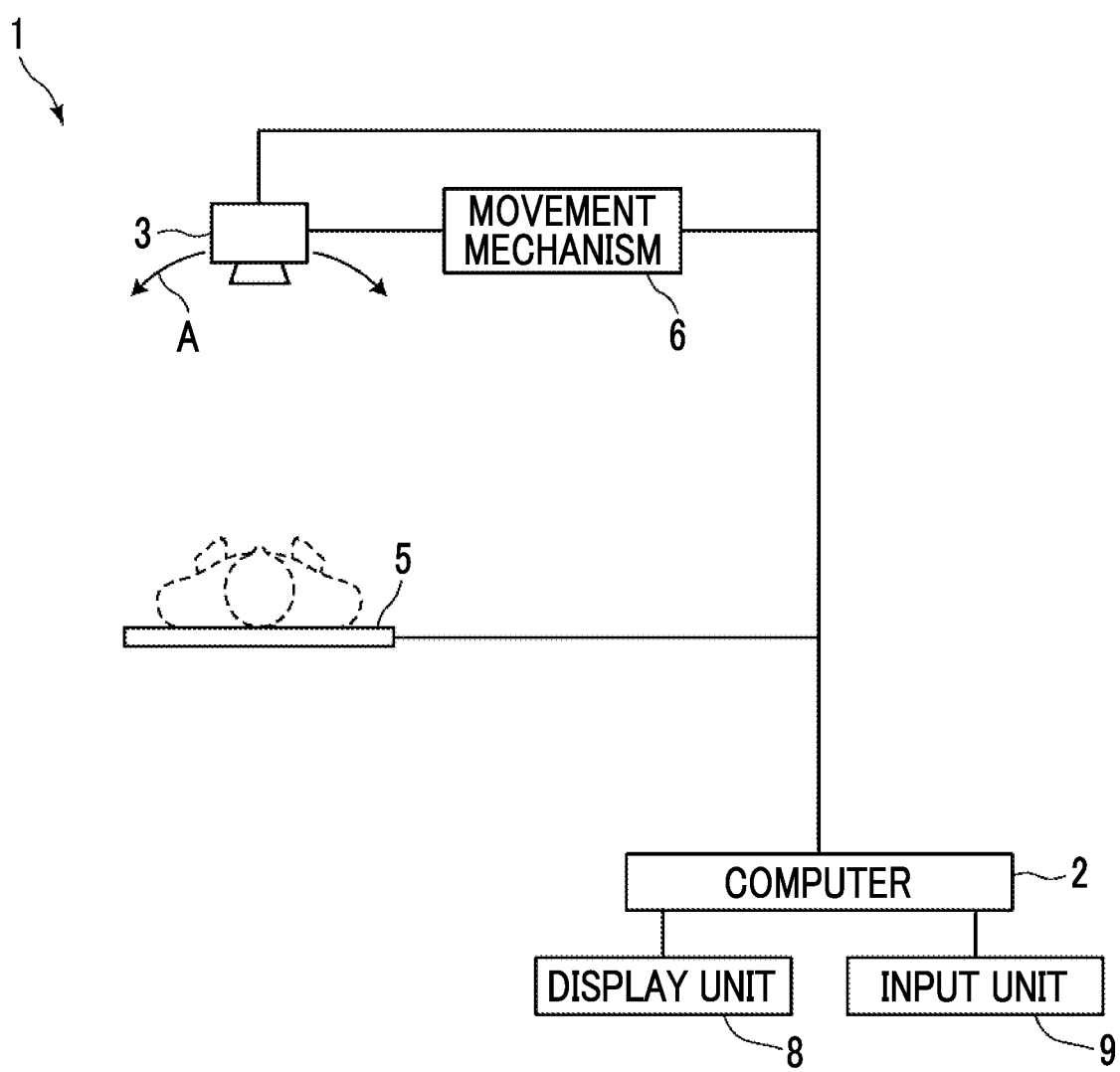
FIG. 1 is a block diagram schematically illustrating the configuration of a radiography system to which a bone mineral information acquisition apparatus according to an embodiment of the present disclosure is applied.

Hereinafter, an embodiment of the present disclosure will be described with reference to the drawings. FIG. 1 is a block diagram schematically illustrating the configuration of a radiography system to which a bone mineral information acquisition apparatus according to the embodiment of the present disclosure is applied. As illustrated in FIG. 1, the radiography system according to this embodiment images a subject H to acquire a radiographic image, and acquires bone mineral information using the acquired radiographic image. The radiography system comprises an imaging apparatus 1 and a computer 2 including the bone mineral information acquisition apparatus according to this embodiment.

The imaging apparatus 1 is for performing tomosynthesis imaging, and includes an X-ray source 3, a radiation detector 5, and a movement mechanism 6 for the X-ray source 3. In FIG. 1, a photographing table for supporting a subject H is omitted. The X-ray source 3 is moved along a circular arc or a straight line by the movement mechanism 6, and irradiates the subject H with X-rays at a plurality of positions on the movement path. In the embodiment, it is assumed that the X-ray source 3 is moved along a circular arc as indicated by an arrow A in FIG. 1. The details of tomosynthesis imaging will be described later. A plurality of radiographic images acquired by tomosynthesis imaging are input to the computer 2 which is a bone mineral information acquisition apparatus. In this embodiment, in a case in which an image of the subject H is captured, a scattered ray removal grid that removes scattered ray components of the X-rays transmitted through the subject H is not used. Therefore, the plurality of radiographic images include primary ray components and scattered ray components of the X-rays transmitted through the subject H.

The radiation detector 5 can repeatedly perform the recording and reading of radiographic images and may be a direct-type radiation detector that is directly irradiated with radiation and generates charge or an indirect-type radiation detector that converts radiation into visible light and then converts the visible light into a charge signal. In addition, it is preferable to use a thin film transistor (TFT) reading method that turns on and off a TFT switch to read a radiographic image signal or a light reading method that emits reading light to read a radiographic image signal as a radiographic image signal reading method. However, the invention is not limited thereto, and other methods may be used.

A display unit 8 and an input unit 9 are connected to the computer 2. The display unit 8 is, for example, a cathode ray tube (CRT) or a liquid crystal display and assists the input of radiographic images acquired by imaging and various types of data required for processes performed in the computer 2. The input unit 9 is, for example, a keyboard, a mouse, or a touch panel.

A bone mineral information acquisition program according to this embodiment is installed in the computer 2. In this embodiment, the computer may be a workstation or a personal computer that is directly operated by an operator or may be a server computer that is connected to the workstation or the personal computer through a network. The bone mineral information acquisition program is recorded on a recording medium, such as a digital versatile disc (DVD) or a compact disc read only memory (CD-ROM), is distributed, and is installed in the computer from the recording medium. Alternatively, the bone mineral information acquisition program is stored in a storage device of a server computer connected to the network or a network storage so as to be accessed from the outside and is downloaded and installed in the computer if necessary.

Figure 2:
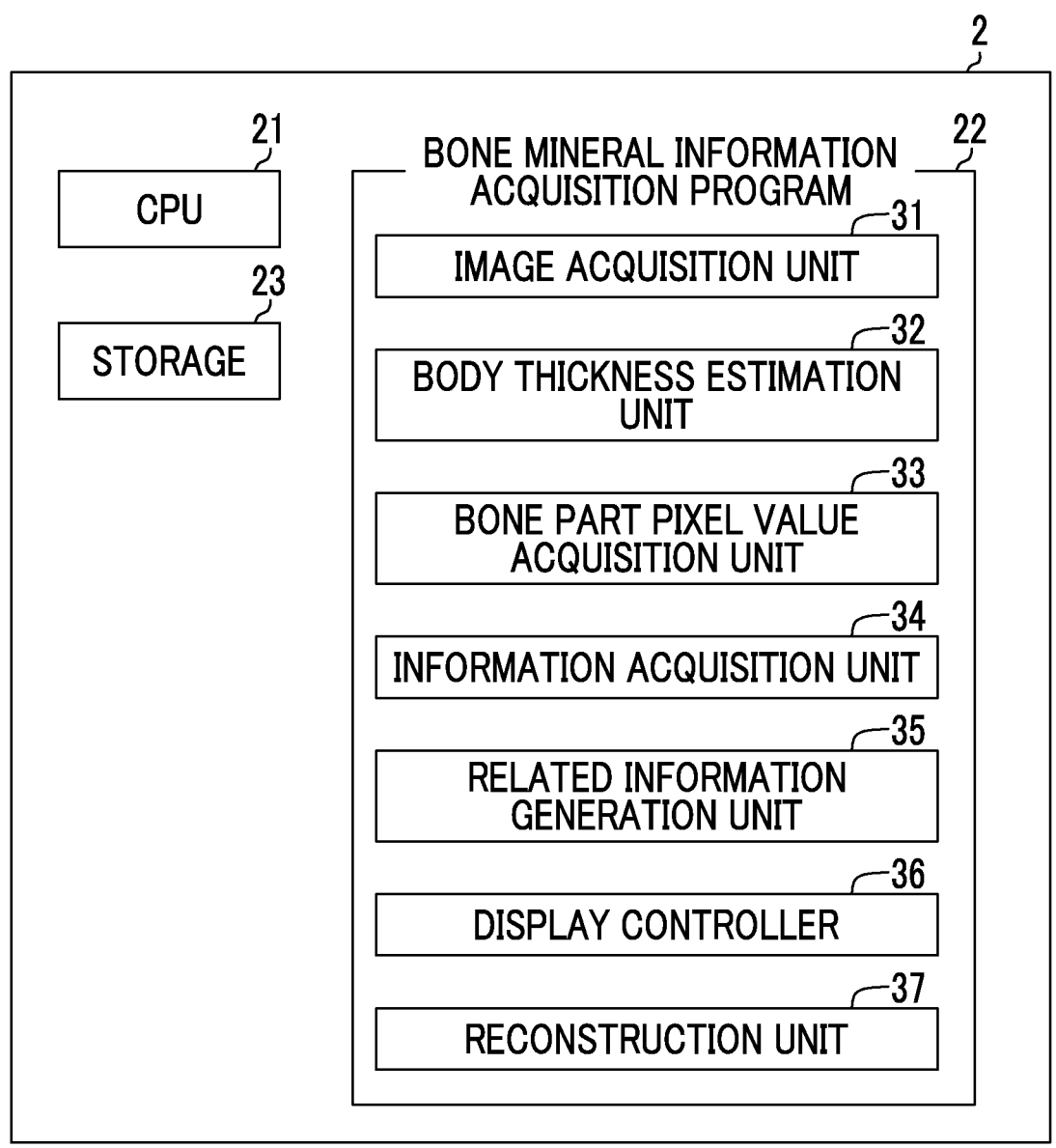
FIG. 2 is a diagram schematically illustrating the configuration of the bone mineral information acquisition apparatus according to this embodiment.

FIG. 2 is a diagram schematically illustrating the configuration of the bone mineral information acquisition apparatus implemented by installing the bone mineral information acquisition program in the computer 2 in this embodiment. As illustrated in FIG. 2, the bone mineral information acquisition apparatus comprises a central processing unit (CPU) 21, a memory 22, and a storage 23 as the configuration of a standard computer.

The storage 23 is a storage device, such as a hard disk drive or a solid state drive (SSD), and stores various kinds of information including programs for driving each unit of the imaging apparatus 1 and the bone mineral information acquisition program. In addition, the storage 23 also stores a plurality of radiographic images Gi acquired by imaging.

For example, the programs stored in the storage 23 are temporarily stored in the memory 22 in order to cause the CPU 21 to perform various processes. The bone mineral information acquisition program defines, as processes performed by the CPU 21, an image acquisition process of causing the imaging apparatus 1 to perform imaging to acquire a plurality of radiographic images each of which includes primary ray components and scattered ray components, a body thickness estimation process of estimating the body thickness of the subject H for each pixel of at least one radiographic image on the basis of the at least one radiographic image among the plurality of radiographic images, a bone part pixel value acquisition process of acquiring a bone part pixel value which is a pixel value of a bone region of the subject H, on the basis of at least one radiographic image, an information acquisition process of acquiring bone mineral information indicating the bone mineral content of the bone region for each pixel of the bone region on the basis of imaging conditions in a case in which at least one radiographic image has been acquired, the body thickness for each pixel, and the bone part pixel value, a related information generation process of generating related information that is related to the bone mineral information, a display control process of displaying the related information on the display unit, and a reconstruction process of generating a tomographic image by reconstructing a plurality of radiographic images.

Then, the CPU 21 performs these processes according to the bone mineral information acquisition program to make the computer 2 function as an image acquisition unit 31, a body thickness estimation unit 32, a bone part pixel value acquisition unit 33, an information acquisition unit 34, a related information generation unit 35, a display controller 36, and a reconstruction unit 37. In addition, in this embodiment, the CPU 21 executes the bone mineral information acquisition program to function as each unit. However, in addition to the CPU 21, a programmable logic device (PLD) that is a processor whose circuit configuration can be changed after manufacture, such as a field programmable gate array (FPGA), can be used as a general-purpose processor that executes software to function as various processing units. Further, the process of each unit may be performed by a dedicated electric circuit, such as an application specific integrated circuit (ASIC), which is a processor having a dedicated circuit configuration designed to perform a specific process.

One processing unit may be configured one of the various processors or a combination of two or more processors of the same type or different types (for example, a combination of a plurality of FPGAs or a combination of a CPU and an FPGA). In addition, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by one or more of the various processors as a hardware structure.

In addition, specifically, the hardware structure of the various processors is an electric circuit (circuitry) obtained by combining circuit elements such as semiconductor elements.

The image acquisition unit 31 moves the X-ray source 3 by driving the movement mechanism 6, irradiates the subject H with X-rays at a plurality of radiation source positions by the movement of the X-ray source 3, and causes the imaging apparatus 1 to perform tomosynthesis imaging for detecting the X-rays passed through the subject H with the radiation detector 5, thereby acquiring a plurality of radiographic images Gi (i=1 to n, n is the number of radiation source positions, for example, n=15) at a plurality of radiation source positions. At this time, imaging conditions, such as the type of a target and a filter used in the X-ray source 3, an imaging dose, a tube voltage, and an SID are set. The imaging conditions may be set by an input operation of the operator through the input unit 9. The set imaging conditions are stored in the storage 23. In this embodiment, it is assumed that an image of the abdomen of the subject H is captured from the chest side and a plurality of radiographic images Gi of the abdomen are acquired from the chest side. In addition, the movement mechanism 6 may be any known mechanism.

Figure 3:
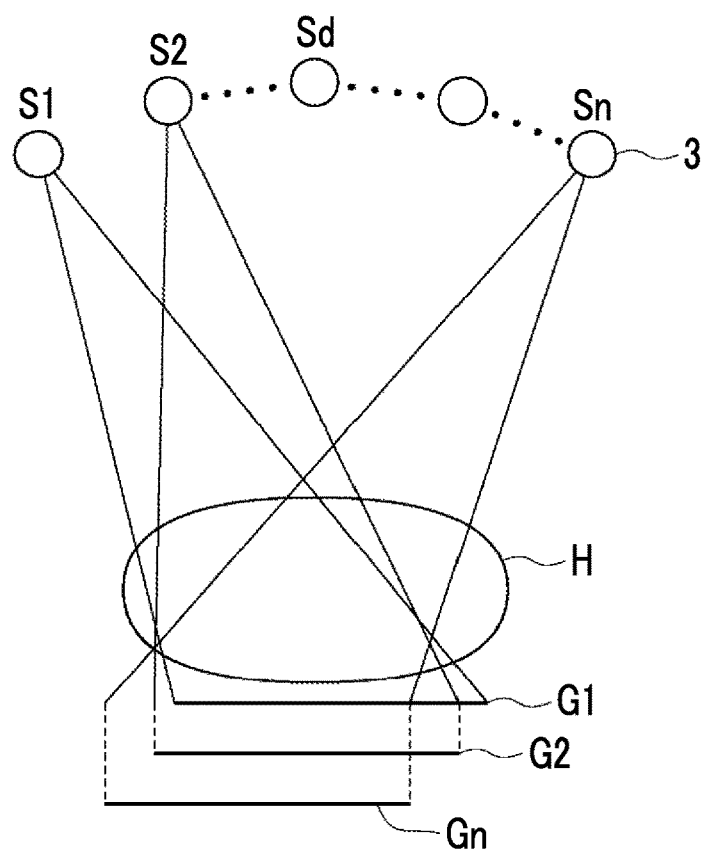
FIG. 3 is a diagram for describing tomosynthesis imaging.

FIG. 3 is a diagram for describing tomosynthesis imaging. As illustrated in FIG. 3, the image acquisition unit 31 moves the X-ray source 3 to each of radiation source positions S1, S2, . . . , and Sn by the movement mechanism 6, drives the X-ray source 3 at each radiation source position to irradiate the subject H with X-rays, and detects X-rays passed through the subject H by the radiation detector 5, thereby acquiring radiographic images G1, G2, . . . , and Gn corresponding to the radiation source positions S1 to Sn. In each of the radiation source positions S1 to Sn, the subject H is irradiated with X-rays of the same dose. The plurality of acquired radiographic images Gi are stored in the storage 23. In addition, the plurality of radiographic images Gi may be acquired by a program separate from the bone mineral information acquisition program and then stored in the storage 23. In this case, the image acquisition unit 31 reads out the plurality of radiographic images Gi stored in the storage 23, from the storage 23 in order to perform processing. In FIG. 3, the radiation source position Sd is a radiation source position at which the optical axis of X-rays from the X-ray source 3 is orthogonal to the radiation detector 5.

Here, the reconstruction unit 37 will be described first. The reconstruction unit 37 reconstructs the plurality of radiographic images Gi to generate a tomographic image in which a desired tomographic plane of the subject H is emphasized. Specifically, the reconstruction unit 37 reconstructs the plurality of radiographic images Gi using a well-known back projection method such as a simple back projection method or a filtered back projection method, and generates a tomographic image Dj (j=1 to m: m is the number of tomographic planes) in each of the plurality of tomographic planes of the subject H.

The body thickness estimation unit 32 estimates the body thickness of the subject H for each pixel of at least one radiographic image on the basis of the at least one radiographic image among the plurality of radiographic images Gi. In the embodiment, it is assumed that the body thickness of the subject H is estimated on the basis of the one radiographic image Gd acquired at the radiation source position Sd. Since the body thickness is estimated for each pixel of the radiographic image Gd, the body thickness estimation unit 32 estimates a body thickness distribution in the radiographic image Gd. In addition, in a case in which the body thickness is estimated, the body thickness estimation unit 32 may generate a low-frequency image indicating a low-frequency component of the radiographic image Gd and may estimate the body thickness using the low-frequency image.

Figure 4:
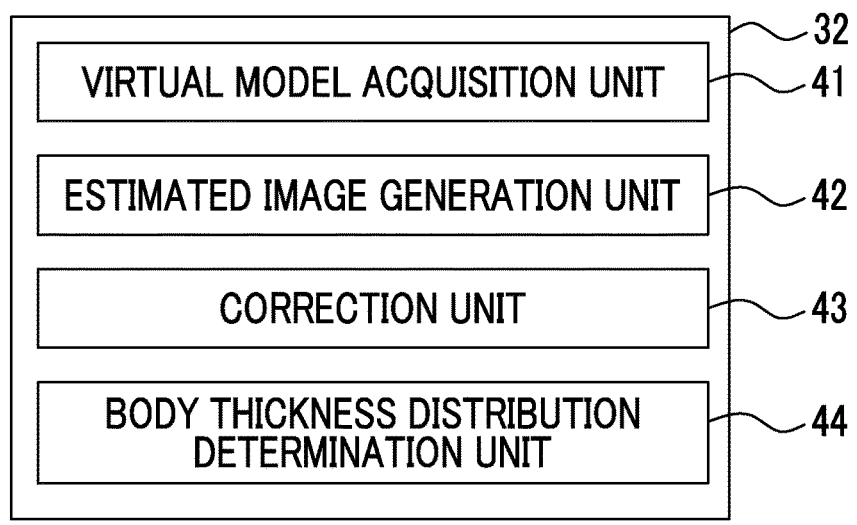
FIG. 4 is a block diagram schematically illustrating the configuration of a body thickness estimation unit.

In this embodiment, the body thickness estimation unit 32 estimates the body thickness of the subject H using, for example, the method disclosed in JP2015-043959A. FIG. 4 is a block diagram schematically illustrating the configuration of the body thickness estimation unit 32. As illustrated in FIG. 4, the body thickness estimation unit 32 comprises a virtual model acquisition unit 41, an estimated image generation unit 42, a correction unit 43, and a body thickness distribution determination unit 44.

The virtual model acquisition unit 41 acquires a virtual model K of the subject H having an initial body thickness distribution T0(x, y). In this embodiment, the virtual model K of the subject H having the initial body thickness distribution T0(x, y) is stored in the storage 23. The virtual model K is data virtually indicating the subject H in which the body thickness following the initial body thickness distribution T0(x, y) is associated with each position on the xy plane.

The estimated image generation unit 42 generates a composite image of an estimated primary ray image obtained by estimating a primary ray image obtained by capturing an image of the virtual model K and an estimated scattered ray image obtained by estimating a scattered ray image obtained by capturing an image of the virtual model K as an estimated image obtained by estimating the radiographic image Gd of the subject H, on the basis of the virtual model K.

The correction unit 43 corrects the initial body thickness distribution T0(x, y) of the virtual model K on the basis of the estimated image and the radiographic image Gd such that a difference between the estimated image and the radiographic image Gd is reduced.

The estimated image generation unit 42 and the correction unit 43 repeat the generation of the estimated image and the correction of the body thickness distribution until the difference between the estimated image and the radiographic image Gd satisfies predetermined end conditions.

The body thickness distribution determination unit 44 determines the body thickness distribution satisfying the end conditions to be the body thickness distribution of the radiographic image Gd, that is, the body thickness T(x, y) for each pixel.

The bone part pixel value acquisition unit 33 acquires the bone part pixel value which is the pixel value of the bone region of the subject H, on the basis of the plurality of radiographic images Gi. Here, the radiographic image Gi includes the bone region and the soft region of the subject H, and the soft region overlaps the bone region. Therefore, the bone part pixel value acquisition unit 33 acquires the pixel value of the bone region from which the influence of the soft region included in the radiographic image Gi has been removed, as the bone part pixel value.

Figure 5:
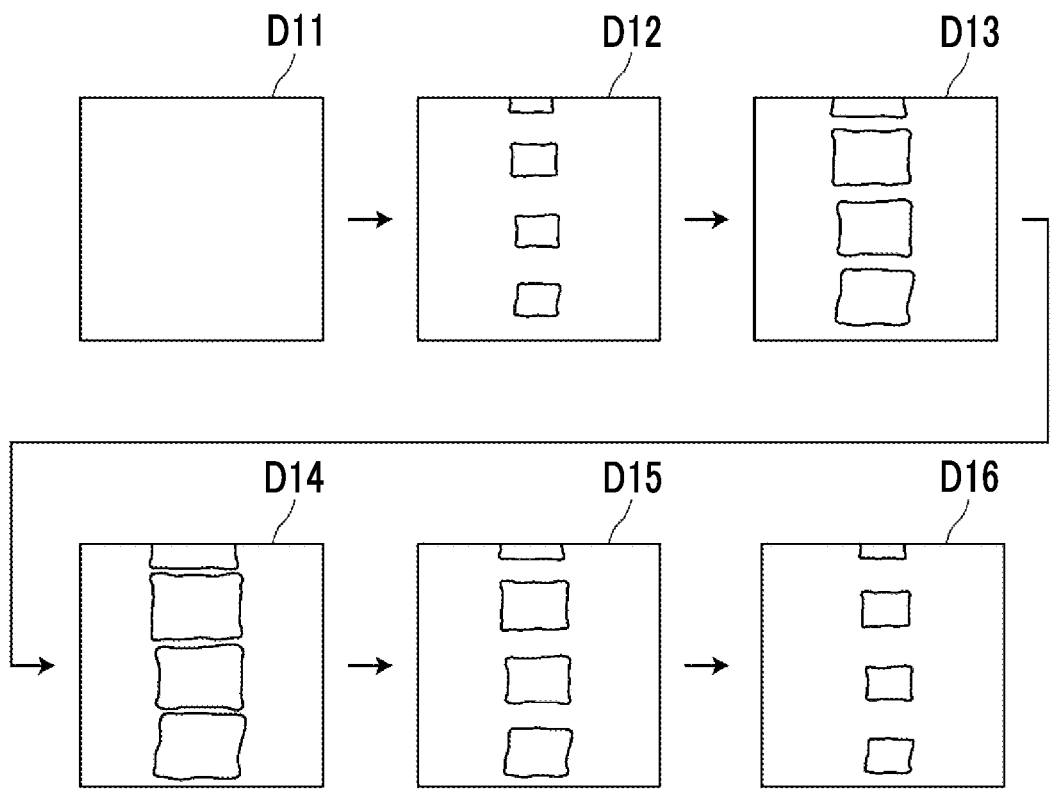
FIG. 5 is a diagram illustrating some tomographic images among a plurality of tomographic images in the order in which the tomographic planes are arranged.

Specifically, the bone part pixel value acquisition unit 33 acquires the bone part pixel value of the subject H using the plurality of tomographic images Dj generated from the plurality of radiographic images Gi by the reconstruction unit 37. FIG. 5 is a diagram illustrating some tomographic images among a plurality of tomographic images Dj in the order in which the tomographic planes are arranged. In FIG. 5, six tomographic images D11 to D16 including only some vertebrae of the spine included in the tomographic image Dj are illustrated for simplicity of explanation. Further, in FIG. 5, tomographic images of tomographic planes of the subject H are illustrated in the order from the tomographic plane closest to the X-ray source 3 to the tomographic plane away from the X-ray source 3. Therefore, the tomographic images D11 to D16 represent tomographic planes from the ventral side to the dorsal side of the subject H. As illustrated in FIG. 5, although the tomographic image D11 does not include a vertebra, the tomographic image D12 of the next tomographic plane includes a tomographic plane of a part close to the ventral surface of the vertebrae. The tomographic image D13 of the next tomographic plane includes a tomographic plane of the vertebrae at a position on the dorsal side of the tomographic image D12. Therefore, in the tomographic image D13, the tomographic plane of the vertebrae becomes larger than that of the tomographic image D12.

The tomographic image D14 includes a tomographic plane of the vertebrae at a position on the dorsal side of the tomographic image D13. Therefore, in the tomographic image D14, the tomographic plane of the vertebrae becomes larger than that of the tomographic image D13. The next tomographic image D15 includes a tomographic plane of the vertebrae at a position on the dorsal side of the tomographic image D14, and the position of the tomographic plane represented by the tomographic image D15 is closer to the dorsal surface than to the ventral surface of the vertebra. Therefore, in the tomographic image D15, the tomographic plane of the vertebrae becomes smaller than that of the tomographic image D14. The next tomographic image D16 includes a tomographic plane of the vertebrae at a position closer to the dorsal surface of the vertebrae than the tomographic plane of the tomographic image D15. Therefore, in the tomographic image D16, the tomographic plane of the vertebrae becomes smaller than that of the tomographic image D15.

Figure 6:
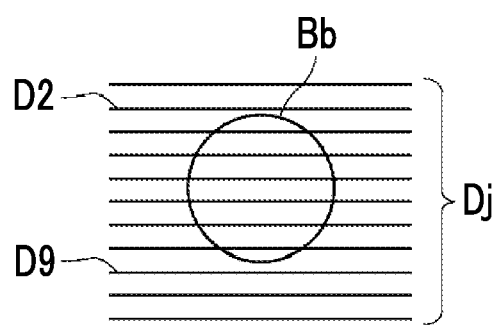
FIG. 6 is a diagram for describing acquisition of the thickness of a bone part.

The bone part pixel value acquisition unit 33 recognizes the bone region in the plurality of tomographic images Dj. Here, the bone region has a lower pixel value than the soft region. For this reason, the bone part pixel value acquisition unit 33 recognizes the bone region in the plurality of tomographic images Dj by thresholding. A discriminator created by machine learning such as deep learning may be used to recognize bone regions in a plurality of tomographic images Dj. Then, the bone part pixel value acquisition unit 33 acquires the thickness of the bone part in a direction in which the tomographic planes of the tomographic images Dj are aligned, using the recognized bone region. FIG. 6 is a diagram for describing acquisition of the thickness of the bone part. In the embodiment, the distance between the tomographic planes of the plurality of tomographic images Dj is known. Therefore, for a bone part Bb included in the subject H, in a case where the bone region of the bone part Bb is recognized in the tomographic images D2 to D9 among the plurality of tomographic images Dj, the bone part pixel value acquisition unit 33 acquires the distance between the tomographic image D2 and the tomographic image D9 as the thickness of the bone part Bb.

The bone part pixel value acquisition unit 33 acquires the bone part pixel value which is the pixel value of the bone region of the subject H, on the basis of the acquired thickness of the bone part. Here, imaging conditions (types of targets and filters for determining the energy of X-rays, tube voltages, imaging doses, and the like) of a plurality of radiographic images Gi acquired by tomosynthesis imaging in the embodiment are known. In the embodiment, the relationship among the pixel value of the bone region in the radiographic image (that is, the pixel value of the bone region in the radiographic image Gi acquired by the image acquisition unit 31), the thickness of the bone part, and the bone part pixel value according to the various imaging conditions, in particular, the various targets/filters and the various tube voltages, is stored in the storage 23 as a table. The bone part pixel value acquisition unit 33 recognizes the bone region in at least one radiographic image among the plurality of radiographic images Gi. In the embodiment, it is assumed that the bone region in one radiographic image Gd is recognized. The recognition of the bone region in the radiographic image Gd may be performed by thresholding, or may be performed by using a discriminator created by machine learning such as deep learning.

Then, the bone part pixel value acquisition unit 33 acquires a table corresponding to the imaging conditions in a case in which the radiographic image Gd has been acquired, from the storage 23, and refers to the acquired table to acquire the bone part pixel value from the thickness of the bone part and the pixel value of the bone region recognized in the radiographic image Gd. Therefore, the bone part pixel value is acquired for each pixel of the radiographic image Gd. Instead of the table, an arithmetic expression for calculating the bone part pixel value from the pixel value of the bone region and the thickness of the bone part in the radiographic image may be stored in the storage 23 in accordance with the various imaging conditions. In this case, the bone part pixel value acquisition unit 33 acquires an arithmetic expression corresponding to the imaging conditions from the storage 23 and acquires a bone part pixel value.

Note that the bone part pixel value may be acquired for each of the plurality of radiographic images Gi, the statistical value of the bone part pixel values may be calculated between corresponding pixels in the plurality of radiographic images Gi, and the calculated statistical value may be used as a final bone part pixel value. In addition, for example, the mean, median, maximum value, or minimum value can be used as the statistical value.

In the embodiment, for example, the method described in JP2015-043959A may be used to generate the tomographic image Dj and acquire the bone part pixel value after removing the scattered ray components from the radiographic image Gi.

The information acquisition unit 34 acquires bone mineral information indicating the bone mineral content of the bone region for each pixel of the bone region included in at least one radiographic image among the plurality of radiographic images Gi. In the embodiment, the information acquisition unit 34 acquires the bone mineral information by converting the acquired bone part pixel value for the radiographic image Gd into a pixel value of the bone part of the radiographic image acquired on the basis of a reference imaging condition, from which the influence of the soft part has been removed.

Figure 7:
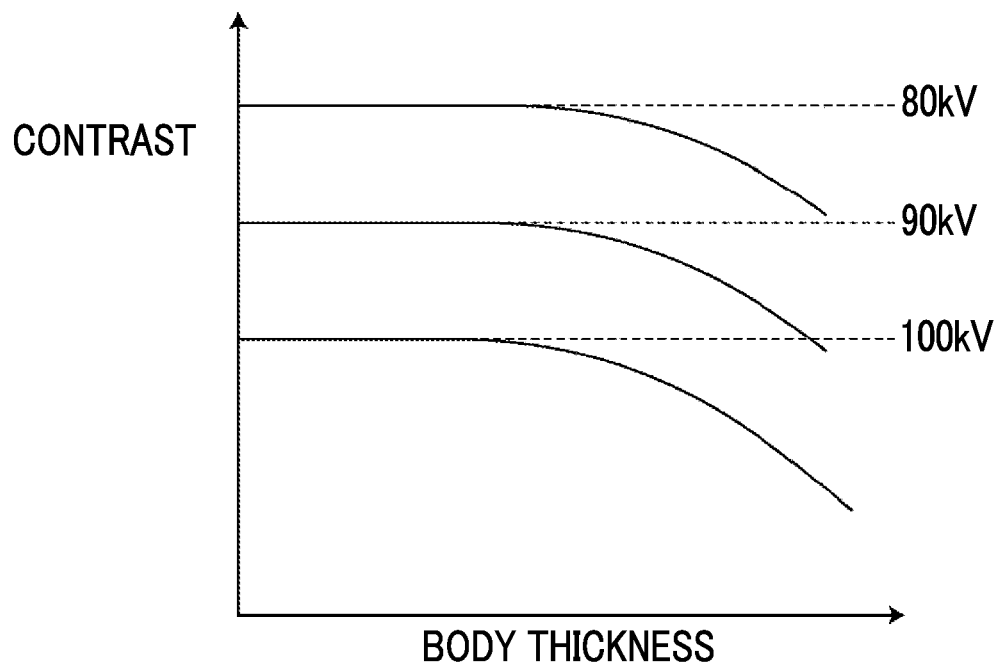
FIG. 7 is a diagram illustrating the relationship between the body thickness and the contrast of the bone part and a soft part.

Here, as the tube voltage applied to the X-ray source 3 becomes higher and the energy of X-rays becomes higher, the contrast of the soft part and the bone part in the radiographic image Gd becomes lower. While X-rays are transmitted through the subject H, beam hardening in which low-energy components of the X-rays are absorbed by the subject H and the energy of the X-rays increases occurs. An increase in the energy of the X-rays due to the beam hardening becomes larger as the body thickness of the subject H becomes larger. FIG. 7 is a diagram illustrating the relationship between the body thickness and the contrast of the bone part and the soft part. In addition, FIG. 7 illustrates the relationship between the body thickness and the contrast of the bone part and the soft part at three tube voltages of 80 kV, 90 kV, and 100 kV. As illustrated in FIG. 7, as the tube voltage becomes higher, the contrast becomes lower. In addition, in a case in which the body thickness is greater than a certain value, as the body thickness becomes larger, the contrast becomes lower. The larger the bone part pixel value in the radiographic image Gd and the larger the bone part pixel value acquired by the bone part pixel value acquisition unit 33, the larger the contrast of the bone part and the soft part. Therefore, the relationship illustrated in FIG. 7 shifts to a higher contrast side as the bone part pixel value becomes larger.

Figure 8:
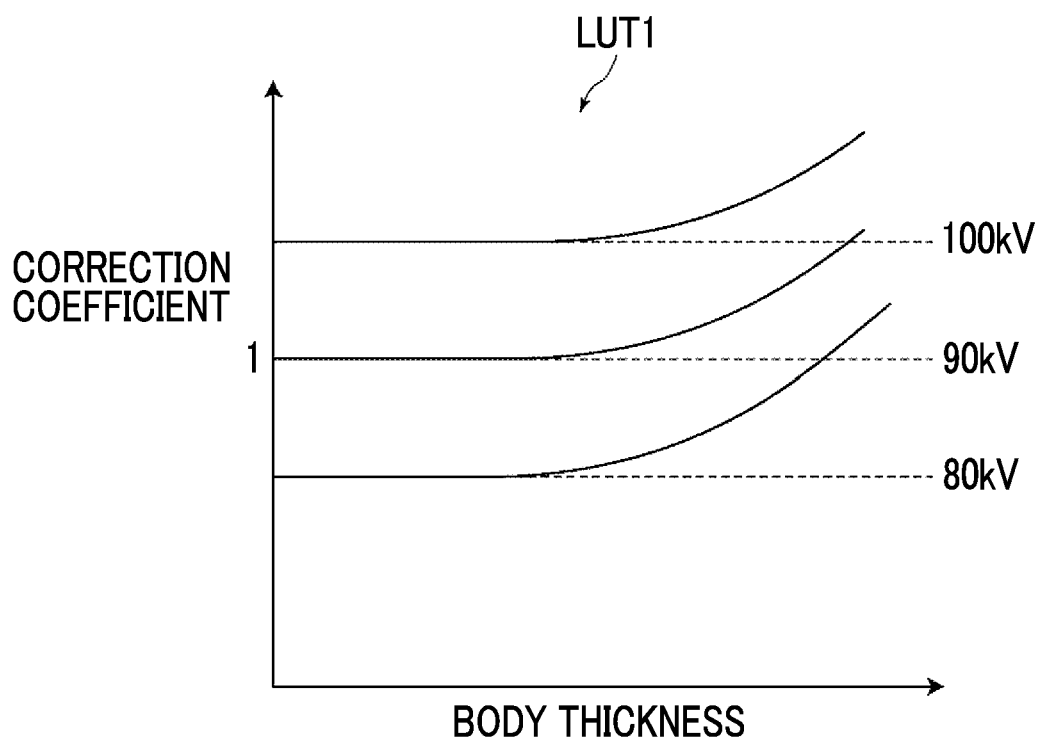
FIG. 8 is a diagram illustrating a look-up table for acquiring a correction coefficient.

In this embodiment, a look-up table in which the reference imaging condition is set to, for example, a tube voltage of 90 kV is prepared. The look-up table is used to acquire a correction coefficient for correcting a difference in contrast depending on a tube voltage at the time of imaging and a reduction in contrast caused by the influence of beam hardening. In addition, the look-up table is stored in the storage 23. FIG. 8 is a diagram illustrating the look-up table for acquiring the correction coefficient. As illustrated in FIG. 8, in a look-up table LUT1, as the tube voltage becomes higher and the body thickness becomes larger, the value of the correction coefficient becomes larger. In this embodiment, the reference imaging condition is a tube voltage of 90 kV. Therefore, in a case in which the tube voltage is 90 kV and the thickness is 0, the correction coefficient is 1. In FIG. 8, the look-up table LUT1 is two-dimensionally illustrated. However, the correction coefficient varies depending on the bone part pixel value. Therefore, in practice, the look-up table LUT1 is a three-dimensional table including an axis indicating the bone part pixel value.

The information acquisition unit 34 acquires a correction coefficient $C0(x, y)$ for each pixel which corresponds to the imaging conditions and the body thickness $T(x, y)$ with reference to the look-up table LUT1. Then, the information acquisition unit 34 multiplies the bone part pixel value $Gb(x, y)$ acquired for the pixel $(x, y)$ of the bone region in the radiographic image Gd by the correction coefficient $C0(x, y)$ to acquire bone mineral information $B0(x, y)$ for each pixel of the bone region of the radiographic image Gd as represented by the following Expression (1). The calculated bone mineral information $B0(x, y)$ is acquired by capturing an image of the subject H at a tube voltage of 90 kV which is the reference imaging condition, and indicates the pixel value in the bone region included in the radiographic image from which the influence of the soft part in the subject H has been removed and the influence of beam hardening has been removed.

$$B0(x,y)=C0(x,y) \times Gb(x,y) \quad (1)$$

In a case in which the image of the subject H is captured, a scattered ray removal grid for removing scattered rays incident on the radiation detector 5 may be used. Therefore, look-up tables corresponding to whether the scattered ray removal grid is present may be prepared and a look-up table for acquiring the correction coefficient may be selected according to whether the scattered ray removal grid is present. In addition, look-up tables corresponding to the types of scattered ray removal grids may be prepared and a look-up table corresponding to the type of scattered ray removal grid used at the time of imaging may be selected.

Figure 9:
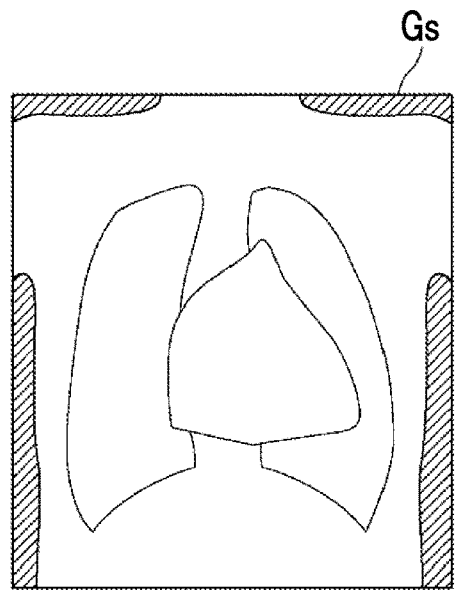
FIG. 9 is a diagram illustrating a soft part image.

The related information generation unit 35 generates related information that is related to the bone mineral information. Therefore, the related information generation unit 35 generates a soft part image Gs indicating the soft part of the subject H on the basis of the body thickness $T(x, y)$ for each pixel of the radiographic image Gd estimated by the body thickness estimation unit 32 and the imaging conditions in a case in which the radiographic image Gd has been acquired. Specifically, the related information generation unit 35 calculates the degree of transmission and scattering of X-rays for each pixel in the radiographic image Gd using the body thickness $T(x, y)$ and the imaging conditions, estimates the dose of X-rays reaching the radiation detector 5, and generates the soft part image Gs by imaging the estimated dose of X-rays. FIG. 9 is a diagram illustrating the soft part image Gs. Then, the related information generation unit 35 generates a composite image Gc obtained by superimposing the bone mineral information B0(x, y) on the soft part image Gs as the related information.

In this embodiment, the bone mineral information may be superimposed on one tomographic image among the plurality of tomographic images Dj to generate the composite image Gc or the bone mineral information B0(x, y) may be superimposed on the one radiographic image (for example, the radiographic image Gd) among the plurality of radiographic images Gi to generate the composite image Gc.

Figure 10:
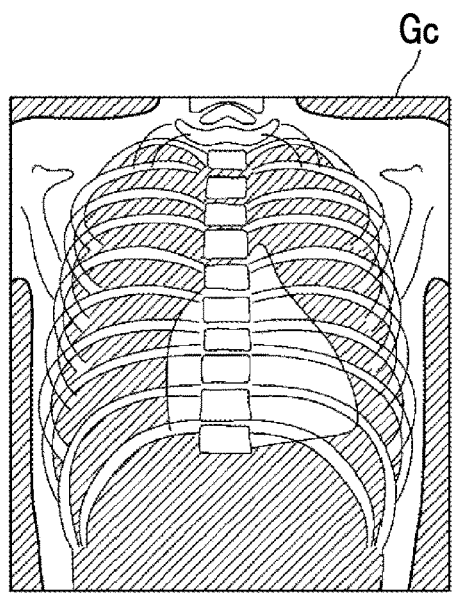
FIG. 10 is a diagram illustrating related information displayed on a display unit.

The display controller 36 displays the related information on the display unit 8. FIG. 10 is a diagram illustrating the related information displayed on the display unit 8. As illustrated in FIG. 10, the related information is the composite image Gc.

Figure 11:
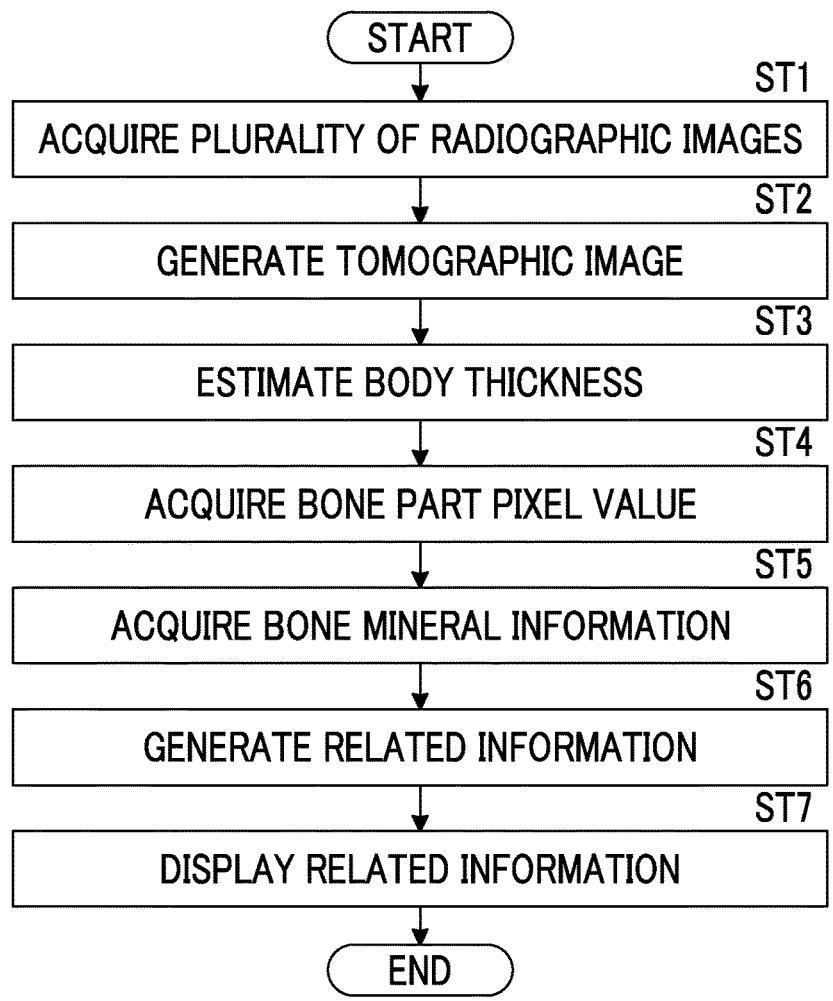
FIG. 11 is a flowchart illustrating a process performed in this embodiment.

Next, a process performed in this embodiment will be described. FIG. 11 is a flowchart illustrating the process performed in this embodiment. First, the image acquisition unit 31 directs the imaging apparatus 1 to perform tomosynthesis imaging and acquires the plurality of radiographic images Gi (Step ST1). The reconstruction unit 37 reconstructs the plurality of radiographic images Gi to generate the plurality of tomographic images Dj of the plurality of tomographic planes of the subject H (Step ST2). Next, the body thickness estimation unit 32 estimates the body thickness of the subject H for each pixel of at least one radiographic image on the basis of the at least one radiographic image (Step ST3). The process of Step ST3 may be performed before Step ST2, or the processes of Step ST2 and Step ST3 may be performed in parallel.

Then, the bone part pixel value acquisition unit 33 acquires the bone part pixel value which is the pixel value of the bone region of the subject H, on the basis of at least one radiographic image (Step ST4). Then, the information acquisition unit 34 acquires bone mineral information indicating the bone mineral content of the bone region for each pixel of the bone region on the basis of the imaging conditions in a case in which at least one radiographic image has been acquired, the body thickness for each pixel, and the bone part pixel value (Step ST5). In addition, the related information generation unit 35 generates related information that is related to the bone mineral information (Step ST6) and the display controller 36 displays the related information on the display unit 8 (Step ST7). Then, the process ends.

As such, according to this embodiment, the body thickness of the subject H is estimated for each pixel of at least one radiographic image among the plurality of radiographic images Gi, and the bone part pixel value which is the pixel value of the bone region of the subject H is acquired on the basis of the at least one radiographic image. Then, the bone mineral information indicating the bone mineral content of the bone region is acquired for each pixel of the bone region on the basis of the imaging conditions in a case in which the at least one radiographic image has been acquired, the body thickness for each pixel, and the bone part pixel value. Therefore, it is possible to acquire the bone mineral information without using a dedicated apparatus unlike the DXA method. In addition, since the bone mineral information is acquired for each pixel of the bone region, it is possible to evaluate the bone mineral information for each part of the bone.

In the above-described embodiment, the composite image Gc obtained by superimposing the bone mineral information B0(x, y) on the soft part image Gs is generated as the related information. However, the invention is not limited thereto.

Figure 12:
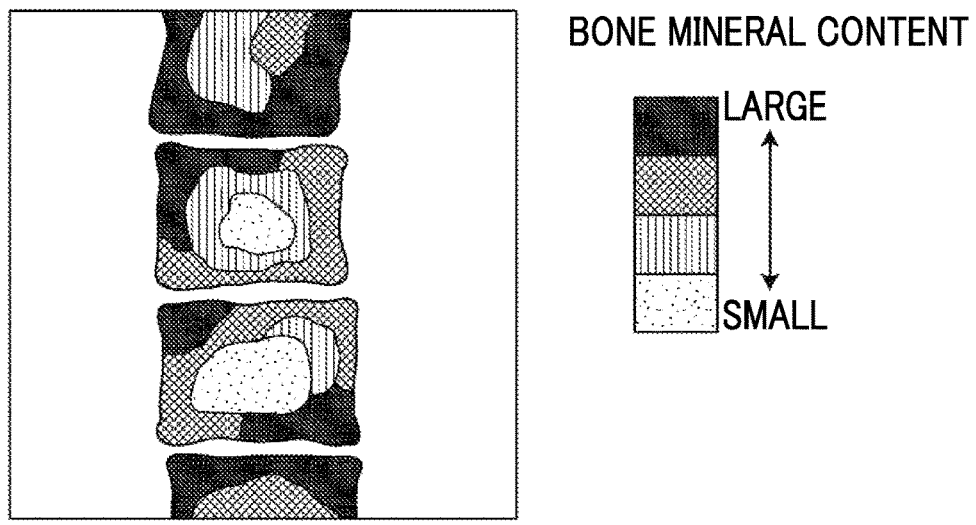
FIG. 12 is a diagram illustrating bone mineral information displayed on the display unit.

The bone mineral information for each pixel acquired by the information acquisition unit 34 may be displayed as the related information. FIG. 12 is a diagram illustrating the bone mineral information displayed on the display unit 8. In addition, FIG. 12 illustrates only some vertebrae of the spine for simplicity of explanation. In this embodiment, since the bone mineral information is calculated for each pixel, the display of the bone mineral information makes it possible to check the distribution of the bone mineral content corresponding to the value of the bone mineral information. In particular, in a case in which different colors are mapped and displayed according to the value of the bone mineral information, it is possible to more easily check the distribution of the bone mineral content. Further, in FIG. 12, the distribution of the bone mineral content is indicated by a difference in hatching.

In addition, the related information generation unit 35 may calculate bone strength from the bone mineral information and may use the calculated bone strength as the related information. In this case, the bone strength can be calculated on the basis of the bone mineral information and an index value indicating bone texture. In addition, the density of a trabecular structure forming the bone is used as the index value indicating the texture. Therefore, the related information generation unit 35 extracts high-frequency components of the image of the bone region in at least one radiographic image among the plurality of radiographic images Gi or at least one tomographic image among the plurality of tomographic images Dj. Any method, such as Fourier transform, wavelet transform, or a method using a high-pass filter, can be used as a method for extracting the high-frequency component. Then, the related information generation unit 35 calculates a variance value of the high-frequency components for each pixel of the bone region. Here, as the density of the trabecular structure becomes lower, the calculated variance value of the high-frequency components becomes smaller. Therefore, the related information generation unit 35 calculates bone strength using the operation of the bone mineral information×the variance value. Here, since the bone mineral information and the variance value are acquired for each pixel of the bone region, the bone strength is also calculated for each pixel.

In addition, texture features by a simultaneous occurrence matrix, such as uniformity, contrast, correlation, or entropy, may be used as the index value indicating the texture. The simultaneous occurrence matrix is a matrix indicating the distribution of signal values of pixels in an image and represents the frequency of the signal value of a pixel adjacent to the pixel having a certain signal value as a matrix.

Figure 13:
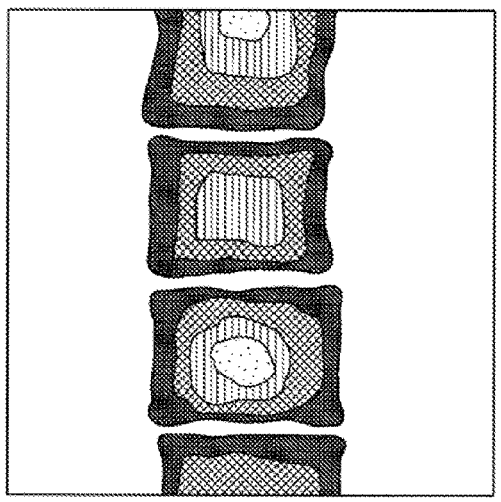
FIG. 13 is a diagram illustrating bone strength displayed on the display unit.
Figure 13:
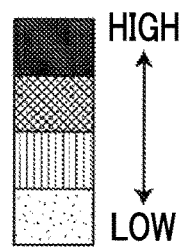

FIG. 13 is a diagram illustrating the bone strength displayed on the display unit 8. FIG. 13 illustrates only some vertebrae of the spine for simplicity of explanation. In this embodiment, since the bone strength is calculated for each pixel, the display of the bone strength makes it possible to check the distribution of the bone strength. In particular, in a case in which different colors are mapped and displayed according to the bone strength, it is possible to more easily check the distribution of the bone strength. Further, in FIG. 13, the distribution of the bone strength is indicated by a difference in hatching.

In a case in which the bone strength is displayed, the bone strength may be displayed so as to be superimposed on the soft part image Gs or may be displayed so as to be superimposed on at least one tomographic image among the plurality of tomographic images Dj. In addition, the bone strength may be displayed so as to be superimposed on at least one radiographic image (for example, the radiographic image Gd) among the plurality of radiographic images Gi.

Figure 14:
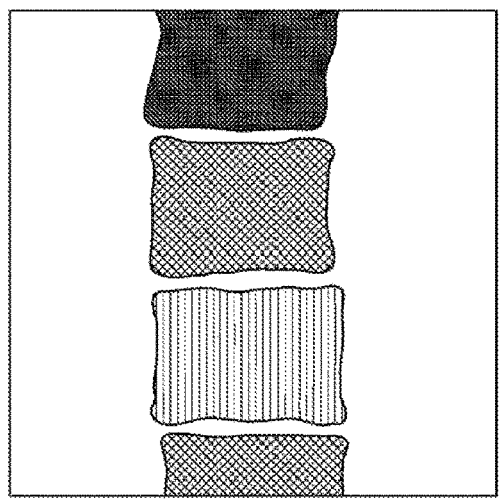
FIG. 14 is a diagram illustrating statistical values of the bone mineral information displayed on the display unit.
Figure 14:
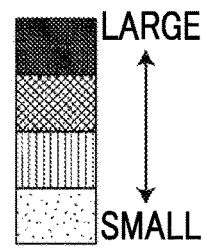

In a case in which a plurality of bones are included in the radiographic image Gi, the related information generation unit 35 may generate the related information for each bone. In this case, a statistical value of bone mineral information for each bone may be used as the related information. In addition, for example, the mean, median, maximum value, and minimum value of the bone mineral information for each bone can be used as the statistical values. FIG. 14 is a diagram illustrating the statistical value of the bone mineral information displayed on the display unit 8. FIG. 14 illustrates only some vertebrae of the spine for simplicity of explanation. In this embodiment, since the statistical value of the bone mineral information is calculated for each bone, it is possible to check the bone mineral information for each bone. In particular, in a case in which different colors are mapped and displayed according to the value of the bone mineral information, it is possible to more easily check the bone mineral information for each bone. Further, in FIG. 14, the difference between the statistical values of the bone mineral information is indicated by a difference in hatching.

Figure 15:
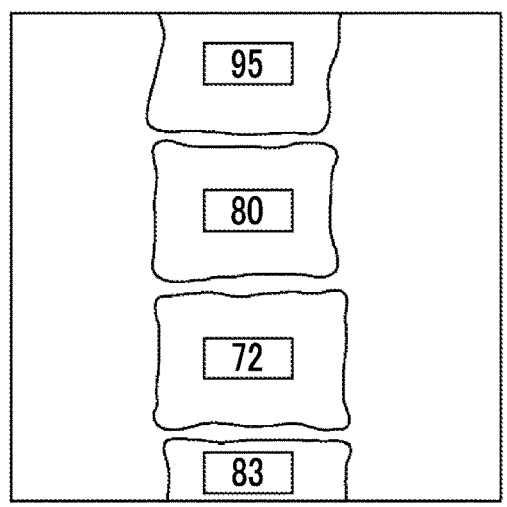
FIG. 15 is a diagram illustrating the statistical values of the bone mineral information displayed on the display unit.

In FIG. 14, the statistical values of the bone mineral information are mapped by different colors corresponding to the magnitudes of the statistical values. However, as illustrated in FIG. 15, the statistical value of the bone mineral information may be displayed as a numerical value.

Figure 16:
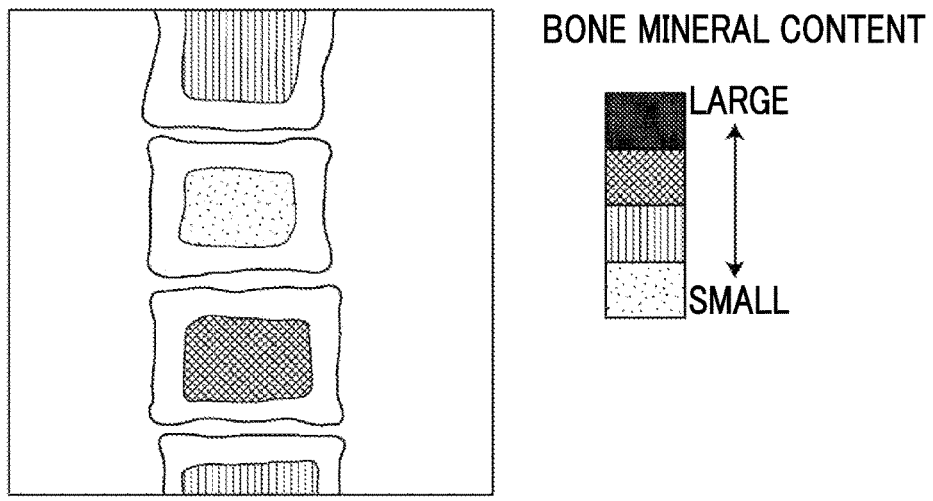
FIG. 16 is a diagram illustrating the statistical values of the bone mineral information of partial regions in the bone region displayed on the display unit.

In addition, the related information generation unit 35 may generate the related information of a partial region in the bone region for one bone. In this case, the statistical value of the bone mineral information of the partial region can be used as the related information. Further, for example, the mean, median, maximum value, and minimum value of the bone mineral information of the partial region can be used as the statistical values. FIG. 16 is a diagram illustrating the statistical value of the bone mineral information of the partial region displayed on the display unit 8. In FIG. 16, for simplicity of explanation, a cancellous bone region is a partial region of the vertebra and the statistical value of the bone mineral information of the cancellous bone region is displayed. In this embodiment, since the statistical value of the bone mineral information is calculated for each bone, it is possible to check the bone mineral information for each bone. In particular, in a case in which different colors are mapped and displayed according to the value of the bone mineral information, it is possible to more easily check the bone mineral information for each bone. Further, in FIG. 16, the difference between the statistical values of the bone mineral information is indicated by a difference in hatching.

As such, since the related information for the cancellous bone region in the bone region is generated, for example, the degree of activation of osteoblasts in the cancellous bone can be checked by medication for osteoporosis. Therefore, it is possible to easily check the effect of medicine treatment.

In FIG. 16, the related information only for the cancellous bone region is generated. However, as illustrated in FIG. 17, the statistical value of the bone mineral information of a cortical bone region in addition to the cancellous bone region may be generated as the related information and then displayed.

Figure 17:
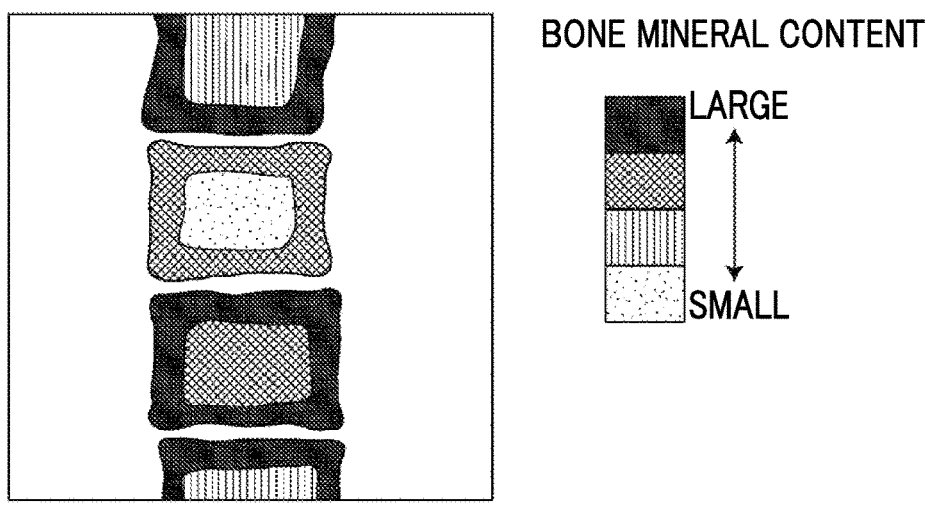
FIG. 17 is a diagram illustrating the statistical values of the bone mineral information of the partial regions displayed on the display unit.
Figure 18:
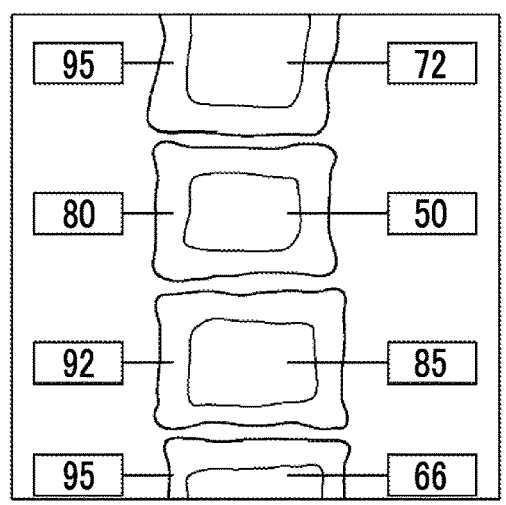
FIG. 18 is a diagram illustrating the statistical values of the bone mineral information of the partial regions displayed on the display unit.

In FIGS. 16 and 17, the statistical values of the bone mineral information calculated for each partial region are mapped by different colors corresponding to the magnitudes of the statistical values. However, as illustrated in FIG. 18, the statistical value of the bone mineral information may be displayed as a numerical value. In addition, in FIG. 18, the numerical values of the statistical values for both the cancellous bone region and the cortical bone region are displayed. However, the numerical value of the statistical value only for the cancellous bone region or only for the cortical bone region may be displayed.

Figure 19:
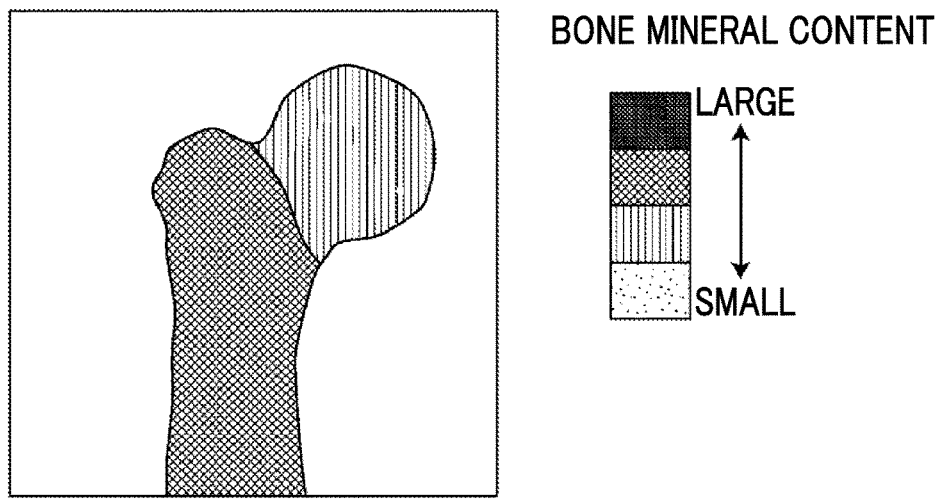
FIG. 19 is a diagram illustrating the statistical values of the bone mineral information of the partial regions displayed on the display unit.

In the above-described embodiment, the bone region is divided into the cortical bone region and the cancellous bone region. However, the invention is not limited thereto. For example, as illustrated in FIG. 19, the femur may be divided into a femoral neck region and the other region, the statistical values of bone mineral information for the regions may be generated as the related information and then displayed. In this case, similarly to FIG. 19, the statistical value of the bone mineral information may be displayed as a numerical value.

Figure 20:
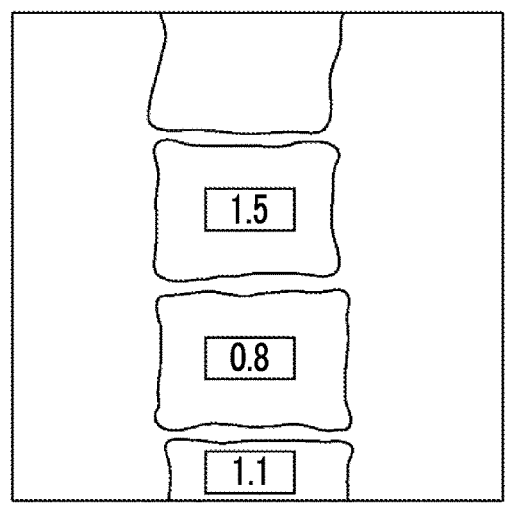
FIG. 20 is a diagram illustrating the comparison result between the statistical values of the bones displayed on the display unit.

In a case in which a plurality of bones are included in the radiographic image Gi, the related information generation unit 35 may generate the comparison result of the bone mineral information between the bones as the related information. In this case, the related information generation unit 35 calculates the statistical value of bone mineral information for each bone and generates, as the related information, a difference value or ratio between the statistical values of the bone mineral information items of a certain bone as a reference bone and other bones. FIG. 20 is a diagram illustrating the comparison result between the statistical values for the bones displayed on the display unit 8. FIG. 20 illustrates only some vertebrae of the spine for simplicity of explanation. The numerical values of the ratios between the statistical values of the bone mineral information items of the uppermost vertebra as a reference vertebra and other vertebrae among the displayed vertebrae are illustrated as the comparison result. As such, since the comparison result of the bone mineral information between the bones is generated as the related information and is then displayed, it is possible to check the bone mineral content of other bones with respect to a certain bone as the reference bone.

Figure 21:
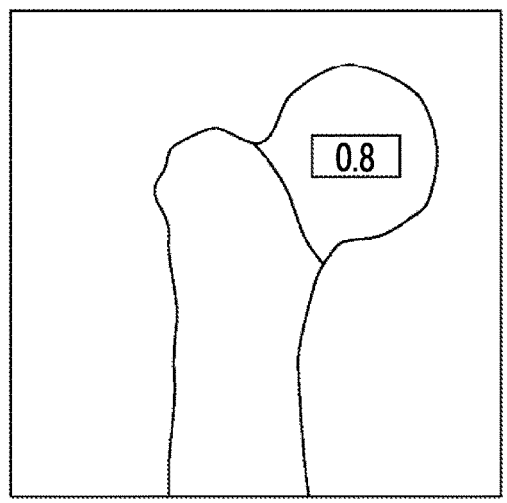
FIG. 21 is a diagram illustrating the comparison result between the statistical values of the partial regions displayed on the display unit.

The related information generation unit 35 may generate, as the related information, the comparison result of the bone mineral information between partial regions in the bone region for one bone. In this case, the related information generation unit 35 calculates the statistical value of the bone mineral information of each partial region in the bone region and generates, as the related information, a difference value or ratio between the statistical values of the bone mineral information items of a certain partial region as a reference partial region and other partial regions. FIG. 21 is a diagram illustrating the comparison result between the statistical values of the partial regions displayed on the display unit 8. FIG. 21 illustrates only a portion of the femur for simplicity of explanation. In addition, the numerical value of the ratio between the statistical values of the bone mineral information items of the region other than the femoral neck region, as the reference partial region, in the displayed femur is illustrated as the comparison result. As such, since the comparison result of the bone mineral information between the partial regions in the bone region is generated as the related information and is then displayed, it is possible to check the bone mineral content of other parts with respect to a certain part in one bone.

In addition, the related information generation unit 35 may generate, as the related information, the comparison result between bone mineral information items acquired for the same subject at different acquisition dates and times. In this case, the related information generation unit 35 calculates the statistical values of the latest bone mineral information and the past bone mineral information for the same subject. The statistical values may be calculated for each bone or the statistical values of all of the bones included in the radiographic image may be calculated. Then, the related information generation unit 35 generates the comparison result between the past statistical value and the latest statistical value as the related information. The ratio or difference value between the past statistical value and the latest statistical value can be used as the comparison result.

Figure 22:
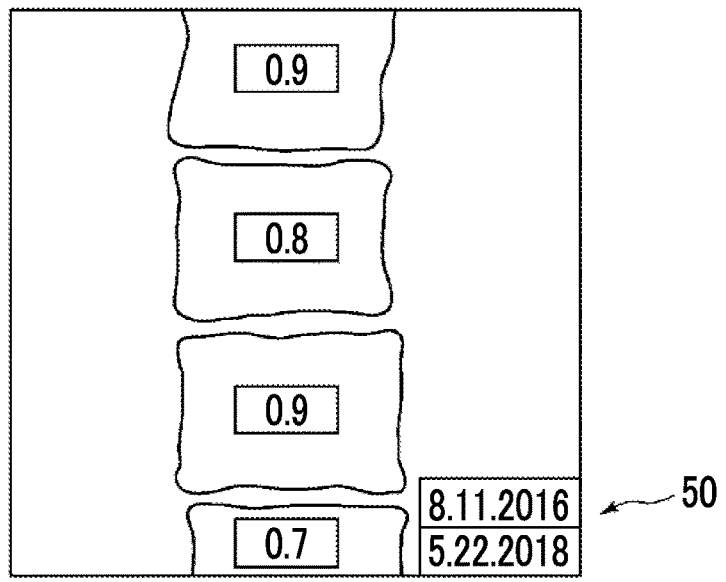
FIG. 22 is a diagram illustrating the comparison result between the bone mineral information items displayed on the display unit.

FIG. 22 is a diagram illustrating the comparison result between the bone mineral information items displayed on the display unit 8. In addition, FIG. 22 illustrates, as the comparison result, the ratio between the statistical values of the past bone mineral information and the latest bone mineral information of each vertebra. Further, FIG. 22 illustrates the date and time when the past bone mineral information was acquired and the date and time 50 when the latest bone mineral information was acquired. As such, since the comparison result between the bone mineral information items acquired from the radiographic images acquired at different dates and times for the same subject is generated as the related information and is then displayed, it is possible to recognize the degree of progress of the disease or the degree of medicine treatment for the subject H. In addition, it is easy to decide a treatment plan on the basis of the degree of progress of the disease or the degree of medicine treatment.

Figure 23:
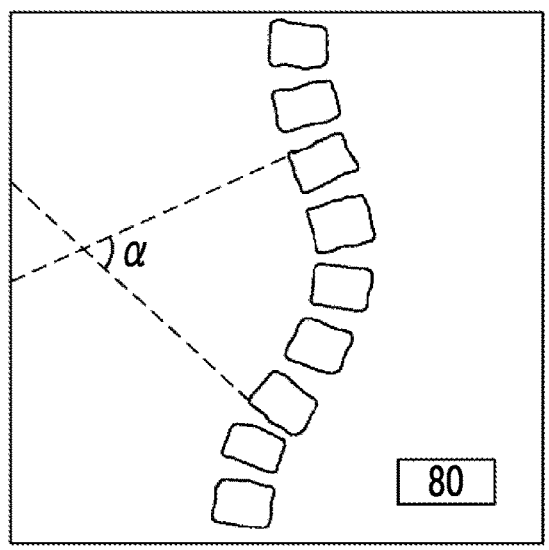
FIG. 23 is a diagram illustrating a bone fracture risk displayed on the display unit.

In a case in which the bone region is the vertebra, the related information generation unit 35 may generate, as the related information, information indicating a bone fracture risk generated from spinal alignment and the bone mineral information. For example, as illustrated in FIG. 23, in a case of a subject suffering from lateral curvature, the related information generation unit 35 calculates a Cobb angle α as the spinal alignment and calculates the bone fracture risk on the basis of the Cobb angle α and the bone mineral information. Here, the Cobb angle is an angle formed between two straight lines that extend from the outer edges of the vertebrae inclined at the maximum angle above and below the vertebra (apical vertebra) which is the apex of the curvature and intersect each other. In addition, the relationship between the bone fracture risk, and the Cobb angle α and the bone mineral information is determined by a table or a computation expression. The related information generation unit 35 calculates the bone fracture risk from the Cobb angle and the bone mineral information with reference to the table or the computation expression. In FIG. 23, the calculated bone fracture risk is illustrated as a numerical value (here, 80). In addition, the bone fracture risk becomes higher as the numerical value becomes larger. As such, since the bone fracture risk is generated as the related information and is then displayed, it is possible to guide a patient who is at high risk of bone fracture such that bone fracture is prevented.

In the above-described embodiment, the display of various kinds of related information has been described. However, a plurality of different related information items may be displayed on the display unit 8 at the same time.

In the above embodiment, the bone mineral information is acquired using a plurality of radiographic images Gi acquired by tomosynthesis imaging, but the present invention is not limited thereto. The image acquisition unit 31 may acquire a plurality of radiographic images generated by irradiating the subject H with X-rays from a plurality of mutually orthogonal directions, and the bone part pixel value acquisition unit 33 may calculate the thickness of the bone part in the imaging direction of one radiographic image among the plurality of radiographic images on the basis of the bone region included in the plurality of radiographic images, and may acquire the bone part pixel value which is the pixel value of the bone region on the basis of the calculated thickness of the bone part.

Figure 24:
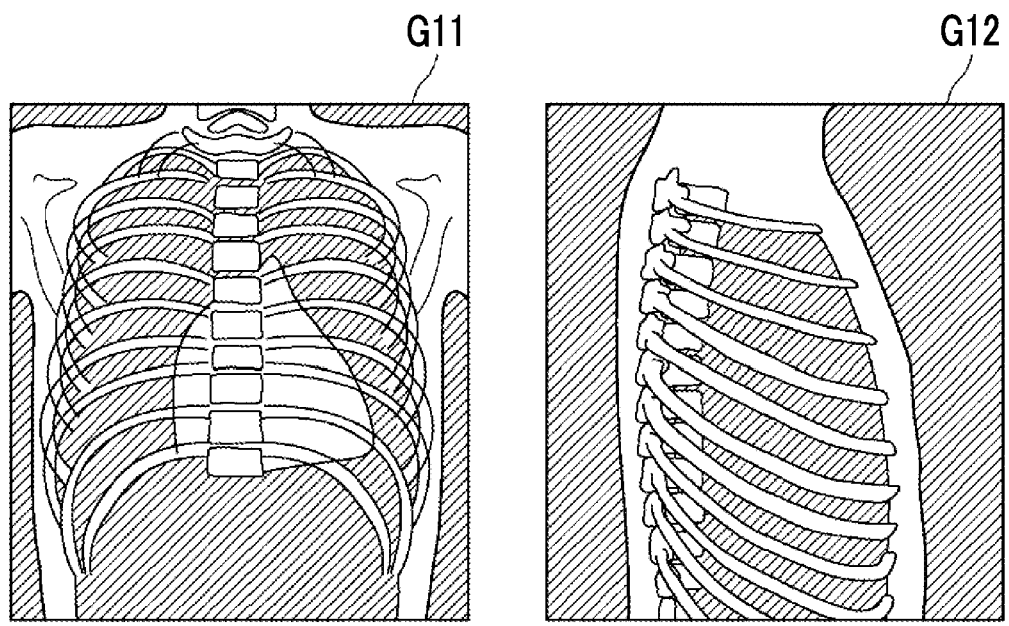
FIG. 24 is a diagram for describing another method for estimating the body thickness.

Here, it is assumed that a first radiographic image G11 obtained by imaging the subject H from the front, and a second radiographic image G12 obtained by imaging the subject H from the side are acquired. FIG. 24 is a diagram illustrating the first radiographic image G11 and the second radiographic image G12. In this manner, by acquiring the first radiographic image G11 obtained by imaging the subject H from the front and the second radiographic image G12 obtained by imaging the subject H from the side, for example, regarding the vertebrae, the same vertebrae included in the first radiographic image G11 and the second radiographic image G12 can be associated with each other. Therefore, regarding a certain vertebra included in the first radiographic image G11, the distance in the direction from the ventral side to the dorsal side of the subject H, that is, the thickness of the vertebra can be acquired by referring to the second radiographic image G12.

The bone part pixel value acquisition unit 33 can also acquire the bone part pixel value for each pixel of the bone region in the first radiographic image G11, which is obtained by imaging the subject H from the front, by acquiring the thickness of the vertebra, that is, the bone part, in the same manner as in the above embodiment. Therefore, in the information acquisition unit 34, the bone mineral information can be acquired from the bone part pixel value.

In the above embodiment, the body thickness estimation unit 32 acquires the body thickness from the radiographic image Gd by using the method disclosed in JP2015-043959A, but the invention is not limited thereto. For example, in the plurality of tomographic images Dj generated by the reconstruction unit 37, a subject region which is a region of the subject H is extracted, and the thickness in the direction in which the tomographic planes of the extracted subject region are arranged is calculated for each pixel of the tomographic image Dj, whereby the body thickness of the subject H can be estimated for each pixel of at least one radiographic image among the plurality of radiographic images Gi.

What is claimed is:

1. A bone mineral information acquisition apparatus comprising:
   a processor configured to:
      estimate a body thickness of a subject including a bone part and a soft part for each pixel of at least one radiographic image among a plurality of radiographic images each of which is acquired by radiations transmitted through the subject and includes a primary ray component and a scattered ray component, on the basis of the plurality of radiographic images;
      acquire a bone part pixel value which is a pixel value of a bone region of the subject, on the basis of the at least one radiographic image; and
      acquire bone mineral information indicating a bone mineral content of the bone region for each pixel of the bone region on the basis of imaging conditions in a case in which the at least one radiographic image has been acquired, the body thickness for each pixel, and the bone part pixel value.

2. The bone mineral information acquisition apparatus according to claim 1, wherein the processor is further configured to:
   move a radiation source relative to a detector, and acquire, as the plurality of radiographic images, a plurality of projection images corresponding to a plurality of radiation source positions by the movement of the radiation source, the projection images being generated by tomosynthesis imaging in which the subject is irradiated with the radiation, at the plurality of radiation source positions; and reconstruct the plurality of radiographic images to generate a plurality of tomographic images of a plurality of tomographic planes of the subject, wherein the processor acquires a thickness of the bone part in a direction orthogonal to the tomographic plane on the basis of the bone region included in the plurality of tomographic images, and acquires the bone part pixel value on the basis of the thickness of the bone part.

3. The bone mineral information acquisition apparatus according to claim 1, wherein the processor is further configured to:

acquire the plurality of radiographic images generated by irradiating the subject with the radiation from a plurality of mutually orthogonal directions, wherein the processor acquires a thickness of the bone part in an imaging direction of one radiographic image among the plurality of radiographic images on the basis of the bone region included in the plurality of radiographic images, and acquires the bone part pixel value on the basis of the thickness of the bone part.

4. The bone mineral information acquisition apparatus according to claim 1, wherein the processor acquires the bone mineral information by converting the bone part pixel value into a pixel value of the bone region included in the radiographic image acquired on the basis of a reference imaging condition.

5. The bone mineral information acquisition apparatus according to claim 4, wherein the reference imaging condition is a tube voltage that is applied to a radiation source in a case in which the at least one radiographic image is acquired.

6. The bone mineral information acquisition apparatus according to claim 4, wherein the processor acquires the bone mineral information by converting the bone part pixel value on the basis of a correction coefficient corresponding to at least one of information on the reference imaging condition, information on beam hardening corresponding to the body thickness, or information on whether a scattered ray removal grid is present during imaging.

7. The bone mineral information acquisition apparatus according to claim 1, further comprising:

a display controller that displays related information, which is related to the bone mineral information, on a display.

8. The bone mineral information acquisition apparatus according to claim 7, wherein the display controller displays, as the related information, a composite image obtained by superimposing the bone mineral information on a soft part image indicating a soft region of the subject or the at least one radiographic image on the display, the soft part image being acquired from the at least one radiographic image.

9. The bone mineral information acquisition apparatus according to claim 7, wherein the display controller displays bone strength calculated from the bone mineral information as the related information on the display.

10. The bone mineral information acquisition apparatus according to claim 7, wherein, in a case in which the subject includes a plurality of bones, the display controller displays the related information acquired for each bone on the display.

11. The bone mineral information acquisition apparatus according to claim 7, wherein the display controller displays the related information on a partial region in the bone region on the display.

12. The bone mineral information acquisition apparatus according to claim 11, wherein the partial region is a cancellous bone region in the bone region.

13. The bone mineral information acquisition apparatus according to claim 7, wherein, in a case in which the subject includes a plurality of bones, the display controller displays a comparison result of the bone mineral information between the bones as the related information on the display.

14. The bone mineral information acquisition apparatus according to claim 7, wherein the display controller displays a comparison result of the bone mineral information between partial regions in the bone region as the related information on the display.

15. The bone mineral information acquisition apparatus according to claim 7, wherein the display controller displays a comparison result between the bone mineral information and past bone mineral information acquired at different dates and times for the same subject as the related information on the display.

16. The bone mineral information acquisition apparatus according to claim 7, wherein, in a case in which the bone region is a vertebra region, the display controller displays, as the related information, information indicating a bone fracture risk which is generated from spinal alignment and the bone mineral information on the display.

17. The bone mineral information acquisition apparatus according to claim 7, wherein the processor is further configured to:

generate the related information.

18. A bone mineral information acquisition method comprising:

estimating a body thickness of a subject including a bone part and a soft part for each pixel of at least one radiographic image among a plurality of radiographic images each of which is acquired by radiations transmitted through the subject and includes a primary ray component and a scattered ray component, on the basis of the plurality of radiographic images;

acquiring a bone part pixel value which is a pixel value of a bone region of the subject, on the basis of the at least one radiographic image; and acquiring bone mineral information indicating a bone mineral content of the bone region for each pixel of the bone region on the basis of imaging conditions in a case in which the at least one radiographic image has been acquired, the body thickness for each pixel, and the bone part pixel value.

19. A non-transitory computer-readable storage medium that stores a bone mineral information acquisition program that causes a computer to perform:

estimating a body thickness of a subject including a bone part and a soft part for each pixel of at least one radiographic image among a plurality of radiographic images each of which is acquired by radiations transmitted through the subject and includes a primary ray component and a scattered ray component, on the basis of the plurality of radiographic images;

acquiring a bone part pixel value which is a pixel value of a bone region of the subject, on the basis of the at least one radiographic image; and acquiring bone mineral information indicating a bone mineral content of the bone region for each pixel of the bone region on the basis of imaging conditions in a case in which the at least one radiographic image has been acquired, the body thickness for each pixel, and the bone part pixel value.

* * * * *